United States Patent [19]

Teraji et al.

[11] 4,381,395

[45] Apr. 26, 1983

[54] PROCESS FOR PREPARING AN IMIDAZOLE DERIVATIVE

[75] Inventors: Tsutomu Teraji, Osaka; Yoshiharu Nakai, Otsu, both of Japan; Graham J. Durant, Welwyn, England

[73] Assignee: SK & F Lab Co., Carolina, P.R.

[21] Appl. No.: 250,796

[22] Filed: Apr. 3, 1981

[51] Int. Cl.³ ............................................ C07D 233/64
[52] U.S. Cl. .................................................... 548/342
[58] Field of Search ......................................... 548/342

[56] References Cited

U.S. PATENT DOCUMENTS 3,950,333  4/1976  Durant et al. ................... 548/342 X
4,128,658  12/1978  Price et al. ........................... 424/285

OTHER PUBLICATIONS

March, J., *Advanced Organic Chemistry*, McGraw Hill, New York, 1968, p. 294.
Derwent Abstract 18809X (Belgian 832,665).
Derwent Abstract 09733D (WP 8100109).

*Primary Examiner*—Richard A. Schwartz
*Attorney, Agent, or Firm*—Joan S. Keps; Richard D. Foggio; Alan D. Lourie

[57] ABSTRACT

This invention relates to new processes for preparing an imidazole derivative, i.e. cimetidine, by (1) reacting an imidazolylmethylthioethylamine with an amidine or (2) reacting a N-cyano-N'-imidazolylmethylthioethyl formamidine with methylamine or (3) reacting a N-methyl-N'-imidazolylmethylthioethyl formamidine with cyanamide.

2 Claims, No Drawings

PROCESS FOR PREPARING AN IMIDAZOLE DERIVATIVE

This invention relates to new processes for preparing an imidazole derivative of the formula:

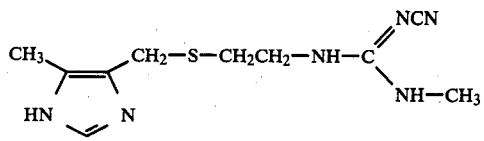

The compound of the formula (I) obtained by this invention is N''-cyano-N'-methyl-N'-8 2-(5-methylimidazoyl-4-ylmethylthio)ethyl]guanidine which is cimetidine which is known as a compound having histamine $H_2$-antagonist activity and is known to be useful as an anti-ulcer agent.

The processes of this invention are illustrated by the following schemata.

Process: 1

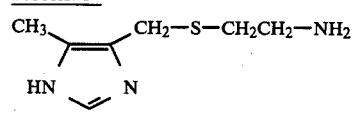

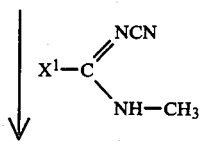

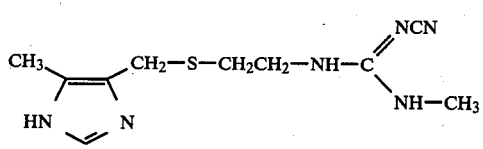

Process: 2

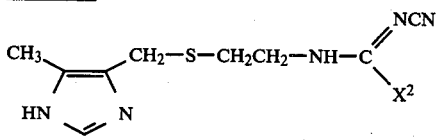

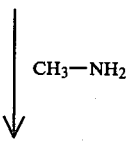

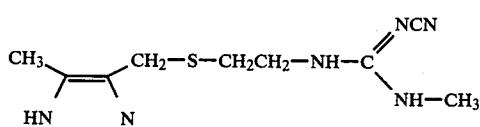

Process: 3

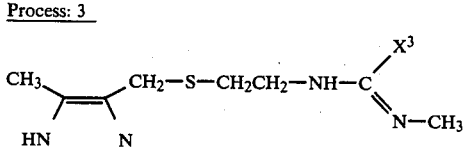

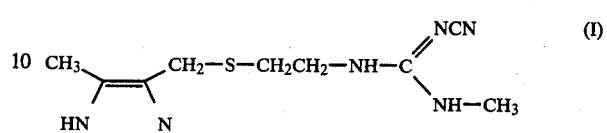

$X^1$ is halogen, mercapto, an aromatic 5-membered N-containing heterocycle-N-yl group or a group of the formula: $-S(O)_n-Z$ in which Z is hydroxy or alkyl, and n is 1 or 2;

$X^2$ is halogen, mercapto, cyanamide, an aromatic 5-membered N-containing heterocycle-N-yl group or a group of the formula: $-S(O)_n-Z$ in which Z and n are each as defined above; and $X^3$ is halogen or a group of the formula; $-S(O)_n-Z$ in which Z and n are each as defined above.

Among the processes of this invention, the Process 1 can be carried out by reacting compound (II) with a compound (III).

As to the starting material (III), the halogen for $X^1$ may be chlorine, bromine and iodine. The aromatic 5-membered N-containing heterocycle-N-yl group for $X^1$ may be 1-pyrazolyl, 1-imidazolyl, 1-pyrrolyl, 1,2,3-triazol-1-yl, 3,5-dimethyl-1-pyrazolyl, 1,2,4-triazol-4-yl or the like. The group of the formula: $-S(O)_n-Z$ for $X^1$ may be sulfino, sulfo, alkyl-sulfinyl having 1 to 6 carbon atoms (e.g. methylsulfinyl, ethylsulfinyl, propylsulfinyl, isopropylsulfinyl, butylsulfinyl, isobutylsulfinyl, tert-butylsulfinyl, pentylsulfinyl, hexylsulfinyl etc.), or alkylsulfonyl having 1 to 6 carbon atoms (e.g. methylsulfonyl, ethylsulfonyl, propylsulfonyl, isopropylsulfonyl, butylsulfonyl, isobutylsulfonyl, tert-butylsulfonyl, pentylsulfonyl, hexylsulfonyl, etc.).

The reaction of this process may be generally carried out in a conventional solvent such as alcohol (e.g. methanol, ethanol, propanol, butanol, isopropyl alcohol, etc.), acetonitrile, methylene chloride, dimethylformamide, dimethylsulfoxide, dioxane, tetrahydrofuran, and the like. The reaction temperature is not critical and the reaction is generally carried out at room temperature to the boiling point of the solvent.

In case that the compound (III) wherein $X^1$ is halogen, sulfino or sulfo group is used as a starting material, the reaction is preferably carried out in the presence of a base such as triethylamine, pyridine, N-methylaniline, 1,5-diazabicyclo[5.4.0] undec-5-ene and the like.

And in case that the compound (III) wherein $X^1$ is a mercapto group is used as a starting material, the reaction is preferably carried out in the presence of a compound of heavy metal (e.g. mercury, silver, lead, etc.).

The compound (III) wherein $X^1$ is a sulfino or sulfo group may be used in a form of a salt such as an alkali metal salt (e.g. sodium salt, potassium salt, etc.), 1,5-diazabicyclo[5.4.0]undec-5-ene salt, and the like.

The aforementioned Process 2 may be carried out by reacting a compound (IV) with methylamine (compound (V)).

As to the starting compound (IV), halogen, an aromatic 5-membered N-containing heterocycle-N-yl group and the group of the formula: $-S(O)_n-Z$ for $X^2$ may be the same as those illustrated in the above Process 1, respectively.

The reaction of this process may be carried out in a solvent as exemplified in the above Process 1, and generally under cooling or at room temperature.

The aforementioned Process 3 may be carried out by reacting a compound (VI) with cyanamide (VII) or its salt.

As to the starting compound (VI), halogen and the group of the formula: $-S(O)_n-Z$ for $X^3$ may be the same as those as exemplified in the aforementioned Process 1, respectively.

Suitable salt of the cyanamide (VII) may be an alkali metal salt such as sodium salt, potassium salt, and the like.

The reaction of this process may be generally effected in a conventional solvent such as methylene chloride, acetonitrile, dimethylformamide, or the like.

The reaction temperature is not critical, and generally the reaction may be carried out under warming or heating.

In case that the cyanamide (VII) is used in a free form as a starting material, the reaction is preferably carried out in the presence of a base as exemplified in the aforementioned Process 1.

The imidazole derivative (I) produced by the processes of this invention may be isolated and purified, and if desired, converted into its salt such as hydrochloride in a conventional manner.

The starting materials to be used in the processes of this invention can be prepared by the method described in the following examples or by a method similar thereto.

The following examples illustrate this invention in more detail.

EXAMPLE 1

(1) To a stirred suspension of N-cyano-N',S-dimethylisothiourea (60 g) in CHCl$_3$ (600 ml) was added a solution of chlorine (82.6 g) in CHCl$_3$ (500 ml) over 30 min. at 0°–5° C. After stirring for 1.5 hrs. at the same temperature, the solvents were evaporated under a reduced pressure and the residue was washed with dry benzene and dried in vacuum. The resulting white powder was dissolved in hot dry acetone (250 ml). After filtration of the insoluble impurities, the filtrate was passed through a short column of SiO$_2$ (60 g) and eluted with CH$_2$Cl$_2$. The eluate was dried up under a reduced pressure and the residue was recrystallized from acetonpetroleum ether to give N-cyano-N'-methylchloroformamidine (36.8 g). Yield 67.4%.

The resultant was recrystallized twice from benzene-acetone to obtain a white crystal, m.p. 130.5°–131.5° C.

Anal. Calcd. for C$_3$H$_4$ClN$_3$: C, 30.60; H, 3.43; N, 35.75; Cl, 30.16. Found: C, 30.69; H, 3.25; N, 35.63; Cl, 29.82.

IR (nujol) $\nu$ max: 3240, 3020, 2220, 1625, 1540, 1403, 1318, 1272, 1257, 1172, 1095, 1048, 1020, 733, 722 cm$^{-1}$.

H-NMR (CD$_3$OD) $\delta$ 2.92 (s, 3H).

(2) To a stirred solution of 2-(5-methylimidazol-4-ylmethylthio)ethylamine (1.0 g) and triethylamine (0.71 g) in methanol (20 ml) was added N-cyano-N'-methylchloroformamidine (0.82 g) and stirred for 7.5 hrs. at 50°–55° C. After evaporation, the residue was subjected to chromatography on SiO$_2$ [eluant: CHCl$_3$-MeOH (10:1)]. The resulting crude product was added to water (3 ml) and extracted repeatedly with ethyl acetate. Ethyl acetate extracts were dried over anhydrous MgSO$_4$ and concentrated under a reduced pressure to small volume. The resulting crystals were collected by filtration and washed with ethyl acetate to give N''-cyano-N-methyl-N'-[2-(5-methylimidazol-4-ylmethylthio)ethyl]guanidine (0.33 g). Yield 22.4%, m.p. 134°–137° C.

EXAMPLE 2

A suspension of N-cyano-N'-methylthiourea (DBU salt) (0.534 g), 2-(5-methylimidazol-4-ylmethylthio)ethylamine (1.03 g), HgO (0.868 g) and anhydrous sodium sulfate (2 g) in CH$_3$CN (20 ml) was heated under reflux for 20 hrs. with vigorous stirring. The hot reaction mixture was filtered and the filtrate was dried up and subjected to chromatography on SiO$_2$ [eluant: CH$_3$CN-CH$_3$OH (4:1)]. The resulting crude product was purified by preparative thin layer chromatography [SiO$_2$, AcOEt—MeOH—28% aq. NH$_3$ (10:1:1)] and recrystallized from CH$_3$CN to give N''-cyano-N-methyl-N'-[2-(5-methylimidazol-4-ylmethylthio)ethyl]guanidine (38.4 mg). Yield 7.6%, m.p. 136°–138° C.

EXAMPLE 3

(1) To a stirred suspension of N-cyano-N',S-dimethylisothiourea (19.4 g) in acetone (700 ml) was added dropwise a solution of m-chloroperbenzoic acid (80% purity, 38.8 g) in acetone (120 ml) at 20°–25° C. After stirring for 1 hr. at the same temperature, the reaction mixture was cooled in an ice bath for 1 hr. and the precipitate was filtered and washed with acetone to give N-cyano-N'-methyl-methylsulfinylformamidine (13.65 g). Yield 62.8%, m.p. 115.5°–116° C.

Anal. Calcd. for C$_4$H$_7$N$_3$OS: C, 33.09; H, 4.86; N, 28.94; S, 22.07. Found: C, 33.08; H, 4.78; N, 28.79; S, 22.14.

IR (nujol) $\nu$ max: 3240, 2200, 1621, 1512, 1418, 1393, 1282, 1173, 1073, 1033, 883, 743 cm$^{-1}$.

NMR (DMSO-d$_6$): $\delta$ 2.82 (s), 2.84 (s).

A small crop (2.60 g, m.p. 112°–112.5° C.) of the same product was further obtained from the filtrate.

(2) A solution of N-cyano-N'-methyl-methylsulfinylformamidine (493 mg) and 2-(5-methylimidazol-4-ylmethylthio)ethylamine (684 mg) in CH$_3$CN (20 ml) was stirred for 4 hrs. at room temperature. After concentration under a reduced pressure, the residue was subjected to chromatography on SiO$_2$ [eluant: CH$_3$CN-CH$_3$OH (4:1)]. The product obtained was recrystallized from CH$_3$CN to give N''-cyano-N-methyl-N'-[2-(5-methylimidazol-4-ylmethylthio)ethyl]guanidine (684 mg). Yield 79.7%, m.p. 136°–138° C.

EXAMPLE 4

(1) To a stirred suspension of NaH (50% oil suspension, 3.58 g) in THF (160 ml) was added pyrazole (5.84 g) at a temperature below room temperature and stirred for 1 hr. To the mixture was added N-cyano-N'-methyl-methylsulfinylformamidine (8.32 g, obtained by the same procedure as in Example 3 (1)) and stirred for 3 hrs. at room temperature. After evaporation under a reduced pressure, the residue was dissolved in water and washed with ether. The aqueous layer was acidified (pH 4) with 10% HCl under ice-cooling. The precipitate was filtered, washed with water and dried to give 1-(N-cyano-N'-methylamidino)pyrazole (7.52 g). An additional amount (0.2 g) of the same product was further obtained from the filtrate. The crude products were combined and recrystallized from ethyl acetate to give the purified product (6.12 g). Yield 71.7%, m.p. 166.5°–168° C.

Anal. Calcd. for $C_6H_7N_5$: C, 48.31; H, 4.73; N, 46.96, Found: C, 48.40; H, 4.69; N, 46.81.

IR (nujol) ν max: 3280, 2200, 1660, 1645, 1540, 1421, 1387, 1348, 1268, 1207, 1173, 1084, 1040, 985, 922, 908, 838, 765, 702 cm$^{-1}$.

NMR (DMSO-$d_6$): δ 3.13 (s, 3H), 6.65 (dd, J=2 Hz, J=3 Hz, 1H), 7.95 (d, J=2 Hz, 1H), 8.53 (d, J=3 Hz, 1H).

(2) A solution of 1-(N-cyano-N'-methylamidino)-pyrazole obtained above (373 mg) and 2-(5-methylimidazol-4-ylmethylthio)ethylamine (503 mg) in $CH_3CN$ (15 ml) was heated under reflux for 24 hrs. The reaction mixture was concentrated under a reduced pressure and the residue was subjected to chromatography on $SiO_2$ [eluant: $CH_3CN$-$CH_3OH$ (4:1)]. The crude product obtained was recrystallized from $CH_3CN$ to give N''-cyano-N-methyl-N'-([2-(5-methylimidazol-4-ylmethylthio)ethyl]guanidine (359 mg). Yield 56.9%, m.p. 137°–138.5° C.

EXAMPLE 5

(1) N-cyano-N'-methylthiourea (DBU salt) (10 g) in water (20 ml) was added to a solution of 35% $H_2O_2$ (21.8 g) and $NaWO_4.2H_2O$ (0.1 g) in water (40 ml) under ice-cooling. After stirring at room temperature for 1.5 hrs., the precipitate was filtered off. The filtrate was concentrated under a reduced pressure and purified by column chromatography [HP-20 resin (Mitsubishi Chem. Ind. Ltd.)] to obtain DBU salt of cyanoiminomethylaminomethanesulfonic acid (1.5 g, 12.7%). The product was further recrystallized from $(CH_3)_2CHOH$ to give purified DBU salt of cyanoiminomethylaminomethanesulfonic acid. m.p. 135°–136° C.

Anal. Calcd. for $C_{12}H_{21}N_5O_3S$: C, 45.70; H, 6.71; N, 22.21; S, 10.16. Found: C, 45.82; H, 6.71; N, 22.20; S, 10.12.

IR (nujol) ν max: 3290, 3160, 2190, 1650, 1608, 1523, 1460, 1415, 1380, 1325, 1263, 1232, 1215, 1203, 1105, 1060, 1028, 1003, 727 cm$^{-1}$.

(2) A solution of cyanoimino-methylaminomethanesulfonic acid (DBU salt) (0.70 g) and 2-(5-methylimidazol-4-ylmethylthio)ethylamine (0.57 g) in ethanol (14 ml) was heated under reflux for 7 hrs. After removal of the solvent under a reduced pressure, the residue was purified by column chromatography on $SiO_2$ [eluant: $CH_3CN$-$CH_3OH$ (4:1)]. After concentration of the eluate under a reduced pressure, the residue was subjected to preparative thin layer chromatography [$SiO_2$, $CH_3COOCH_3$-$CH_3OH$- 28% $NH_3$(aq) (10:1:1)] and then recrystallized from $CH_3OH$-$CH_3CN$ to give N''-cyano-N-methyl-N'-[2-(5-methylimidazol-4-ylmethylthio)ethyl]guanidine (0.18 g). Yield 32.4%, m.p. 140°–141° C.

EXAMPLE 6

(1) To a solution of sodium metal (1.01 g) in ethanol (120 ml) were added cyanamide (18.5 g) and N-cyano-S-methyl-N'-[2-(5-methylimidazol-4-ylmethylthio)ethyl]isothiourea (10.76 g). The resulting mixture was heated under reflux for 1.5 hrs. After concentration under a reduced pressure, the residue was added to cold water (50 ml) and acidified (pH 4.5) with 10% HCl and cooled for 1 hr. in an ice bath. The precipitate was filtered, washed with water and dried. The resulting crude product (7.43 g) was recrystallized from $C_2H_5OH$-$H_2O$ (1:1) to give N,N'-dicyano-N''-[2-(5-methylimidazol-4-ylmethylthio)ethyl]guanidine (5.17 g).

Yield 49.2%, m.p. 183°–186° C.

Anal. Calcd. for $C_{10}H_{13}N_7S$: C, 45.61; H, 4.98; N, 37.24; S, 12.18. Found: C, 45.59; H, 4.99; N, 36.51; S, 12.17.

IR (nujol) ν max: 3330, 3110, 2660, 2170, 1575, 1518, 1435, 1378, 1348, 1310, 1230, 867 cm$^{-1}$.

NMR (DMSO-$d_6$+$D_2O$): δ 2.32 (s, 3H), 2.4-2.7 (m, 2H), 3.26 (t, J=7 Hz, 2H), 3.83 (s, 2H), 8.77 (s, 1H).

(2) N,N'-Dicyano-N'-[2-(5-methylimidazol-4-ylmethylthio)ethyl]guanidine (527 mg) was added to a solution of $CH_3NH_2$ in ethanol (40%, 3.1 g) and stirred for 47 hrs. at room temperature. After concentration under a reduced pressure, the residue was triturated with $CH_3CN$. The insoluble starting material was filtered off and the filtrate was concentrated under a reduced pressure and chromatographed on $SiO_2$ [eluant: $CH_3CN$-$CH_3OH$ (4:1)]. The resulting crude product was purified by preparative thin layer chromatography [$SiO_2$, $CH_3$—$COOC_2H_5$—$CH_3OH$— 28% $NH_3$ (aq) (10:1:1)] and recrystallized from $CH_3CN$ to give N''-cyano-N-methyl-N'-[2-(5-methylimidazol-4-ylmethylthio)ethyl]-guanidine (1.0 mg). m.p. 135°–137° C.

EXAMPLE 7

(1) A solution of 2-(5-methylimidazol-4-ylmethylthio)ethylisothiocyanate [obtained from its hydrochloride (4.17 g)] in $CHCl_3$(20 ml) was added to a solution of cyanamide (1.05 g) and DBU (3.80 g) in $CHCl_3$ (50 ml) and stirred overnight. After concentration, the residue was dissolved in water (30 ml) and washed with ether, decolorized with charcoal and acidified to pH 5 with 10% HCl under ice-cooling. The precipitate was filtered, washed with water and dried to give N-cyano-N'-[2-(5-methylimidazol-4-ylmethylthio)ethyl]thiourea(mono-hydrate, 3.57 g). Yield 78.1%, m.p. 158°–161° C.

Anal. Calcd. for $C_9H_{13}N_5S_2.H_2O$: C, 39.54; H, 5.53; N, 25.62; S, 23.46, Found: C, 39.71; H, 5.44; N, 25.69; S, 22.73.

IR (nujol) ν max: 3400, 3270, 3130, 2760, 2650, 2190, 1652, 1540, 1470, 1430, 1381, 1362, 1278, 1237, 1217, 1205, 1103, 1088, 967, 837 cm$^{-1}$.

NMR (DMSO-$d_6$+$D_2O$): δ 2.32 (s, 3H), 2.4-2.8 (m, 2H), 3.0-3.67 (m, 2H), 3.87 (s, 2H), 8.93 (s, 1H).

(2) To a suspension of N-cyano-N'-[2-(5-methylimidazol-4-ylmethylthio)ethyl]thiourea (monohydrate, 765 mg) in $CH_2Cl_2$ (7 ml) was introduced dry HCl gas for a few minutes under ice-cooling. $PCl_5$ (1.25 g) was added to the mixture and stirred at room temperature for 3 hrs. The reaction mixture containing N'-cyano-N-[2-(5-methylimidazol-4-ylmethylthio)ethyl]-chloroformamidine was concentrated to small volume, diluted with $CH_2Cl_2$ (5 ml) and cooled to $-5°$ C. To the mixture was added a solution of $CH_3NH_2$ in $C_2H_5OH$ (40%, 15 ml) below 30° C. After stirring for 20 hrs. at room temperature, the reaction mixture was filtered and the filtrate was concentrated to small volume, diluted with $CH_3CN$ and filtered agein. The filtrate was dried up and the residue was purified with column chromatography [$SiO_2$, $CH_3CN$-$CH_3OH$ (4:1)], preparative thin layer chromatography [$SiO_2$, $CH_3COOC_2H_5$—$CH_3OH$— 28% $NH_3$(aq) (10:1:1)] and then recrystallization from $CH_3CN$ to give N''-cyano-N-methyl-N'-[2-(5-methylimidazol-4-ylmethylthio)ethyl]guanidine (10.4 mg). Yield 1.5%, m.p. 136.5°–138° C.

EXAMPLE 8

A solution of N-methyl-chloroformimidoyl chloride (1.12 g), 2-(5-methylimidazol-4-ylmethylthio)ethylamine (0.855 g) and DBU (0.988 g) in CH₂Cl₂ (16 ml was heated under reflux for 6 hrs. To the reaction mixture containing N'-methyl-N-[2-(5-methylimidazol-4-ylmethylthio)ethyl]chloroformamidine was added a solution of cyanamide (0.84 g) and DBU (3.04 g) in CH₂Cl₂ (16 ml). After refluxing for 15 hrs., the solvent was removed and the residue was chromatographed [SiO₂, CH₃CN-CH₃OH (4:1)]. The crude product was purified by preparative chromatography [SiO₂, CH₃COOC₂H₅—CH₃OH— 28% NH₃(aq) (10:1:1)] and then recrystallization from CH₃CN to give N"-cyano-N-methyl-N'-[2-(5-methylimidazol-4-ylmethylthio)ethyl]guanidine (0.24 g). Yield 19.0%, m.p. 139°–141° C.

What is claimed is:

1. A process for preparing an imidazole derivative of the formula:

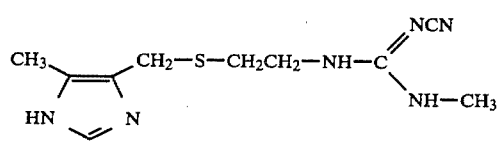

which comprises (1) reacting a compound of the formula:

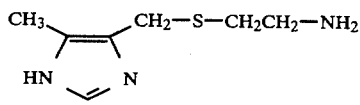

with a compound of the formula:

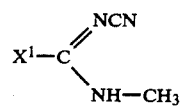

wherein $X^1$ is an aromatic 5-membered N-containing heterocycle-N-yl or a group of the formula: $-S(O)_n-Z$ in which Z is hydroxy or alkyl, and n is 1 or 2, provided that $X^1$ is not a pyrazolyl ring; or (2) reacting a compound of the formula:

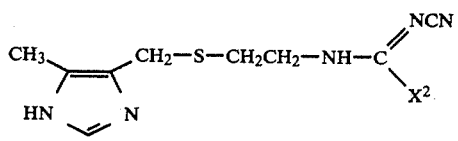

wherein $X^2$ is cyanamide, an aromatic 5-membered N-containing heterocycle-N-yl or a group of the formula: $-S(O)_n-Z$ in which Z is hydroxy or alkyl, and n is 1 or 2, provided that $X^2$ is not a pyrazolyl ring, with methylamine; or (3) reacting a compound of the formula:

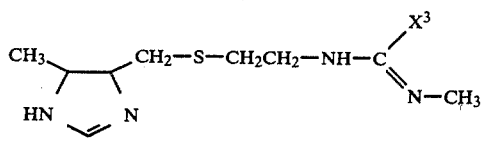

wherein $X^3$ is a group of the formula:
$-S(O)_n-Z$ in which Z is hydroxy or alkyl, and n is 1 or 2,
with cyanamide or a salt thereof.

2. A process according to claim 1 in which $X^1$, $X^2$ and $X^3$ are $-S(O)_n-Z$ in which Z is hydroxy and n is 1 or 2.

* * * * *

UNITED STATES PATENT AND TRADEMARK OFFICE
CERTIFICATE OF CORRECTION

PATENT NO. : 4,381,395
DATED : April 26, 1983
INVENTOR(S) : Tsutomu Teraji, Yoshiharu Nakai and Graham J. Durant It is certified that error appears in the above-identified patent and that said Letters Patent is hereby corrected as shown below:

Column 1, line 16,    N'-methyl-N'-8    2-(5-    should read
    N-methyl-N'-[2-(5-    .

Column 6, line 11,    N,N'-Dicyano-N'-    should read
    N,N'-Dicyano-N"-    .

Column 8, lines 27-32, that portion of the structural formula reading 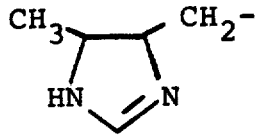    should read 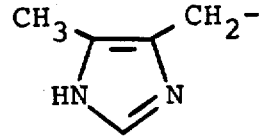

Signed and Sealed this

Second Day of August 1983

[SEAL]

Attest:

GERALD J. MOSSINGHOFF

Attesting Officer    Commissioner of Patents and Trademarks